(12) United States Patent
Weiger

(10) Patent No.: US 9,874,738 B2
(45) Date of Patent: Jan. 23, 2018

(54) ENDOSCOPE WITH IMAGE ERECTING DEVICE

(71) Applicant: Karl Storz GmbH & Co. KG, Tuttlingen (DE)

(72) Inventor: Ulrich Weiger, Kolbingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 14/201,178

(22) Filed: Mar. 7, 2014

(65) Prior Publication Data

US 2014/0254006 A1 Sep. 11, 2014

(30) Foreign Application Priority Data

Mar. 8, 2013 (DE) .......... 10 2013 102 343
Aug. 9, 2013 (DE) .......... 10 2013 108 631

(51) Int. Cl.
*G02B 23/24* (2006.01)
*G02B 23/02* (2006.01)
*A61B 1/00* (2006.01)

(52) U.S. Cl.
CPC ...... *G02B 23/2446* (2013.01); *A61B 1/00183* (2013.01); *G02B 23/02* (2013.01); *G02B 23/243* (2013.01)

(58) Field of Classification Search
CPC .. G02B 23/02; G02B 23/243; G02B 23/2446; A61B 1/00183
USPC ......................................... 359/434
See application file for complete search history.

(56) References Cited

U.S. PATENT DOCUMENTS

| 3,880,148 | A | | 4/1975 | Kanehira et al. |
| 4,641,961 | A | * | 2/1987 | Yamada ............ G01M 11/0235 356/124 |
| 6,560,013 | B1 | * | 5/2003 | Ramsbottom ................. 359/431 |
| 2011/0199471 | A1 | | 8/2011 | Tomioka |

FOREIGN PATENT DOCUMENTS

| DE | 2347914 A1 | 4/1974 |
| DE | 60015375 T2 | 2/2006 |
| DE | 102010010948 A1 | 9/2011 |
| DE | 102010033425 A1 | 2/2012 |
| GB | 1088431 A * | 10/1967 ............... G02B 5/04 |
| GB | 1088431 A | 10/1967 |

* cited by examiner

*Primary Examiner* — Bumsuk Won
*Assistant Examiner* — Wen Huang
(74) *Attorney, Agent, or Firm* — Whitmyer IP Group LLC

(57) ABSTRACT

An endoscope includes an image transmission device in a shaft for transmitting an image from the distal end to the proximal end of the endoscope and an image erecting device for erecting an image registered by means of the endoscope. The image erecting device has a first surface for angle-dependent reflection and a second surface for angle-dependent reflection. The image erecting device is arranged and embodied in such a way that light for image erecting is successively reflected at the first reflective surface, passed through the first reflective surface and through the second, reflective surface and reflected at the second reflective surface.

14 Claims, 3 Drawing Sheets

Fig. 7  A-A
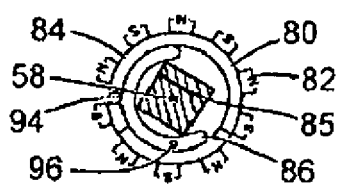
Fig. 8
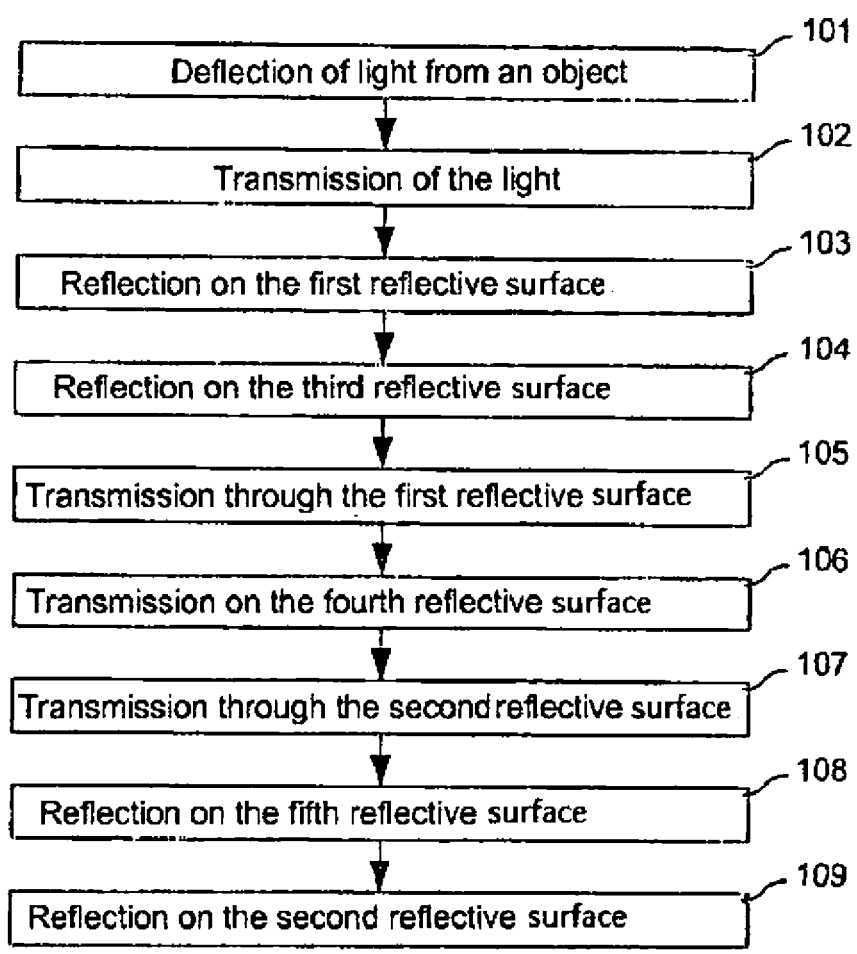

ENDOSCOPE WITH IMAGE ERECTING DEVICE

FIELD OF THE INVENTION

The present invention relates to an endoscope with an image erecting device for erecting an image registered by means of the endoscope, in particular to the configuration of the image erecting device, and to a method for erecting an image in an endoscope.

BACKGROUND OF THE INVENTION

Relay lens systems made of a plurality of rod lenses arranged in succession are used in many rigid endoscopes. Each element of the relay lens system, in particular each rod lens, brings about a complete reversal of the image, i.e. a lateral reversal in both vertical and horizontal direction, equating to a rotation through 180 degrees about the optical axis of the relay lens system. In the case of direct-vision endoscopes or endoscopes with a viewing direction parallel to the longitudinal axis of the shaft, an erect and non-reversed image becomes visible in the eyepiece for the user due to a suitable (in particular odd) number of elements of the relay lens system or rod lenses. This also applies to non-direct-vision endoscopes, which have a Bauernfeind prism or a different arrangement of an even number of coplanar reflective surfaces for deflecting the light emanating from an object.

Endoscopes with an adjustable viewing direction for example only have one reflective surface at the distal end, which reflective surface is pivotable for adjusting the viewing direction (cf., for example, DE 10 2010 010 948 A1). The single reflective surface brings about a lateral reversal in a direction parallel to a plane which contains the surface normal of the reflective surface and the optical axis in front of and behind the reflective surface.

Alternatively, provision is made, for example, for two reflective surfaces at the distal end of the endoscope, of which one is pivotable for adjusting the viewing direction (cf., for example, DE 10 2010 033 425 A1). When pivoting the pivotable reflective surface and hence the viewing direction, the observed image rotates.

For the image erecting or for counter rotating the image, use can be made of a Dove/Amici prism or an Abbe/König prism. Both prisms have specific disadvantages.

SUMMARY OF THE INVENTION

An object of the present invention consists of developing an improved endoscope with an image erecting device and an improved method for erecting an image in an endoscope.

This object is achieved by the subjects of the independent claims.

Developments are specified in the dependent claims.

An endoscope comprises an image transmission device in a shaft for transmitting an image from the distal end to the proximal end of the endoscope and an image erecting device for erecting an image registered by means of the endoscope, the image erecting device having a first surface for angle-dependent reflection and a second surface for angle-dependent reflection, and the image erecting device being arranged and embodied in such a way that light for image erecting is successively reflected at the first reflective surface, passed through the first reflective surface and through the second, reflective surface and reflected at the second reflective surface.

The endoscope can be embodied for medical or for non-medical, in particular technical, applications. The endoscope has a reflective surface, in particular at the distal end of the shaft, for coupling light emanating from an object into the image transmission device. The orientation of the reflective surface defines the viewing direction of the endoscope. In particular, the reflective surface can be pivoted for adjusting the viewing direction of the endoscope.

The image transmission device comprises, in particular, a plurality of rod lenses arranged in succession, or a different relay lens system. Alternatively or additionally, the image transmission device can—particularly if or to the extent that the shaft of the endoscope is flexible—have a coherent bundle of optical fibers. The image transmission transmits the image in the form of light, which emanates from an object to be observed.

The image erecting device can be arranged distally or proximally from the image transmission device or between two parts of the image transmission device (in particular between two rod lenses). The erecting of the image registered by means of the endoscope, caused by the image erecting device, consists in a side reversal in a direction which, in particular, lies in a plane which contains the surface normal of the reflective surface (in the case where the latter is curved: in the center thereof) and the optical axis of the image transmission device.

In particular, both surfaces, for angle-dependent reflection, of the image erecting device are planar in each case. In particular, both surfaces for angle-dependent reflection are arranged in a roof shape.

The configuration of the image erecting device with two surfaces for angle-dependent reflection and, in particular, the arrangement and configuration of the image erecting device in such a way that the light emanating from the object to be observed is successively reflected at the first reflective surface, passed through the first reflective surface and through the second reflective surface and reflected at the second reflective surface can enable a particularly compact configuration of the image erecting device. As emerges from, in particular, the following illustrated further properties and features of the image erecting device and from the description of the embodiments, the image erecting device can have a cross section (in a plane perpendicular to the optical axis of the image transmission device) which is only slightly larger than the beam cross section. The compact configuration of the image erecting device is particularly advantageous if the image erecting device itself is rotatable for counter rotating an image which is rotated about an angle depending on the set viewing direction. Furthermore, the compact configuration can enable an arrangement of the image erecting device at the distal end or at a different location in the shaft of the endoscope.

In the case of an endoscope as is described here, the image erecting device is, in particular, arranged and embodied in such a way that light for image erecting is successively reflected at the first reflective surface, reflected at a third reflective surface, passed through the first reflective surface, reflected at a fourth reflective surface, passed through the second reflective surface, reflected at a fifth reflective surface and reflected at the second reflective surface.

In particular, the third reflective surface, the fourth reflective surface and the fifth reflective surface each reflect independently of the angle and moreover, in particular, are mirrored in each case. In particular, the third reflective surface, the fourth reflective surface and the fifth reflective surface each are planar.

In the case of an endoscope as is described here, the third reflective surface, the fourth reflective surface and the fifth reflective surface are, in particular, arranged parallel to one another.

In the case of an endoscope as is described here, the third reflective surface, the fourth reflective surface and the fifth reflective surface are, in particular, arranged parallel to the optical axis of the image transmission device.

In the case of an endoscope as is described here, all reflective surfaces of the image erecting device, which are involved in the image erecting, are, in particular, planar and coplanar.

All reflective surfaces at which light must be reflected for the image erecting, i.e. at which the light is not only reflected in an edge region of the beam and/or due to manufacturing tolerances or an adjustment error, are involved in the image erecting. The first surface for angle-dependent reflection, the second surface for angle-dependent reflection and the third, fourth and fifth reflective surfaces (each, in particular, for angle-independent reflection) are involved in the image erecting.

In the case of an endoscope as is described here, the image erecting device substantially has the form of a cuboid, the cuboid having a substantially square cross section in a plane perpendicular to the optical axis of the image transmission device.

The form of the image erecting device can deviate from the form of an ideal cuboid, in particular at edges, by virtue of the edges being provided with fibers for protection against damage. Furthermore, the form of the image erecting device deviates from the form of an ideal cuboid by virtue of, in particular, it being possible that the image erecting device is assembled from a plurality of prisms between which narrow gaps and/or steps can be provided on the outer surfaces. Furthermore, the form of the image erecting device can deviate from the form of an ideal cuboid to the extent that the light-entry surface and the light-exit surface of the image device can in each case be curved and/or modified or complemented by rod lenses or other devices with a non-square cross section.

In particular, in the case of an endoscope as is described here, the light-entry surface of the image erecting device and the light-exit surface of the image erecting device are arranged on two planar surface sections, lying opposite one another, of the six planar surface sections of the cuboid, and the fourth reflective surface, on the one hand, and the third and the fifth reflective surface, on the other hand, are arranged on two further planar surface sections, lying opposite one another, of the six planar surface sections of the cuboid.

In the case of an endoscope as is described here, the image erecting device comprises, in particular, a first prism, a second prism and a third prism, the first prism comprising a light-entry surface of the image erecting device, the first reflective surface and the third reflective surface, the second prism comprising the fourth reflective surface, a light-entry surface which is opposite and parallel to the first reflective surface, and a light-exit surface which is opposite and parallel to the second reflective surface, and the third prism comprising a light-exit surface of the image erecting device, the second reflective surface and the fifth reflective surface.

In particular, the first prism and the third prism are similar and arranged symmetrically to one another. Here, the light-entry surfaces of the image erecting device on the first prism and the light-exit surface of the image erecting device on the third prism are of the same size and, in particular, planar and parallel to one another. The third reflective surface on the first prism and the fifth reflective surface on the third prism are, in particular, of the same size, parallel to one another and lie in a common plane. On the first prism, the light-entry surface is, in particular, perpendicular to the third reflective surface. On the third prism, the light-exit surface is, in particular, perpendicular to the fifth reflective surface. The first reflective surface, the second reflective surface, the light-entry surface of the second prism and the light-exit surface of the second prism are, in particular, of the same size or substantially of the same size.

In particular, an edge region of the first reflective surface on the first prism is adhesively bonded to an edge region of the light-entry surface of the second prism and an edge region of the second reflective surface on the third prism is adhesively bonded to an edge region of the light-exit surface of the second prism. Here, an (in particular stop-shaped) spacer in each case defines a predetermined small distance between the first reflective surface on the first prism and the light-entry surface of the second prism, and between the second reflective surface on the third prism and the light-exit surface of the second prism.

The above-described setup of the image erecting device made of three prisms, which are adhesively bonded to one another, in particular in edge regions of surface sections lying opposite one another, enables particularly robust and permanent setting of the three prisms, and hence also of all reflective surfaces, with respect to one another.

In the case of an endoscope as is described here, the first reflective surface and the second reflective surface of the image erecting device are, in particular, each arranged at an angle of 30 degrees with respect to the optical axis of the image transmission device.

In the case of reflection at the first reflective surface, the angle between the light and the surface normal is approximately 60 degrees. After reflection at the first reflective surface, the light impinges on the third reflective surface at an angle of approximately 30 degrees with respect to the surface normal, is reflected there, passes through the first reflective surface parallel to the surface normal, impinges on the fourth reflective surface at an angle of approximately 30 degrees with respect to the surface normal, is reflected there, passes through the second reflective surface parallel to the surface normal, impinges on the fifth reflective surface at an angle of approximately 30 degrees with respect to the surface normal and is reflected at the latter. Finally, the light impinges on the second reflective surface at an angle of approximately 60 degrees with respect to the surface normal and is reflected at this surface.

In particular, an endoscope, as is described here, furthermore comprises a further reflective surface at the distal end of the endoscope, for coupling light, emanating from an object to be observed, into the image transmission device, the further reflective surface being pivotable about a pivot axis for adjusting the viewing direction, and a device for coupling the image erecting device with the further reflective surface in such a way that pivoting the further reflective surface about the pivot axis is accompanied by a rotation of the image erecting device about a rotational axis parallel to the optical axis of the image transmission device.

The orientation of the pivotable further reflective surface defines the viewing direction of the endoscope, wherein pivoting the reflective surface about a certain angle can bring about pivoting of the viewing direction about the same angle, about twice the angle or about a different angle. In particular, the pivot axis of the further reflective surface is orthogonal to the longitudinal axis of the shaft of the endoscope. The device for coupling the image erecting device with the further reflective surface is, in particular, a mechanical device. Alternatively, the device can have an electronic logic or a different digital or analog logic and one or more electric motors, ultrasound motors or other linear or rotational drive devices. In particular, the device for coupling comprises a cam gear for converting a rotational movement of the image erecting device into a translational movement of a push or pull rod or another transmission device for transmitting the translational movement to the pivotable further reflective surface at the distal end of the endoscope. The distal end of the transmission device is e.g. embodied as a connection rod or coupled by means of a connection rod to the pivotable further reflective surface.

In a method for erecting an image in an endoscope, light emanating from an object to be observed is reflected at a first surface for angle-dependent reflection, the light is transmitted through the first surface for angle-dependent reflection, the light is transmitted through a second surface for angle-dependent reflection and the light is reflected at the second surface for angle-dependent reflection.

In particular, the method can be carried out by means of an endoscope as is described herein. The endoscope can be provided and embodied for medical or non-medical or technical applications. In particular, the steps are carried out in the specified sequence.

Before and/or after the above-described steps, the light emanating from the object to be observed can be transmitted from a distal end to a proximal end of the endoscope, in particular by means of a relay lens system and/or a coherent bundle of optical fibers.

In particular, the light emanating from the object to be observed is reflected at a third reflective surface after being reflected at the first reflective surface and prior to being transmitted through the first reflective surface, reflected at a fourth reflective surface after being transmitted through the first reflective surface and prior to being transmitted through the second reflective surface and reflected at a fifth reflective surface after being transmitted through the second reflective surface and prior to being reflected at the second reflective surface. The third reflective surface, the fourth reflective surface and the fifth reflective surface each have, in particular, angle-independent reflection.

In a method as is described here, light emanating from the object to be observed is reflected before all steps described above, in particular by means of a further reflective surface at the distal end of a shaft of the endoscope, wherein the orientation of the further reflective surface defines the viewing direction of the endoscope.

BRIEF DESCRIPTION OF THE DRAWINGS

In the following text, embodiments are explained in more detail on the basis of the attached figures. In detail:

FIG. 7 shows a schematic sectional illustration of an image erecting device and of a magnet support;

FIG. 8 shows a schematic flowchart of a method for erecting an image in an endoscope.

DETAILED DESCRIPTION OF THE INVENTION

Figure 1:
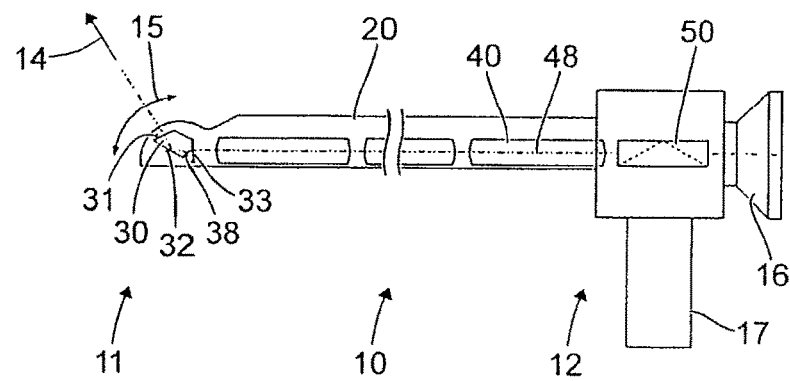
FIG. 1 shows a schematic illustration of an endoscope with an image erecting device.

FIG. 1 shows a schematic illustration of an endoscope 10 with a distal end 11 and a proximal end 12. The viewing direction 14 of the endoscope 10 can be adjusted within a range indicated by a curved arrow 15. At the proximal end 12, the endoscope 10 has an eyepiece 16 and a coupling 17 for a light conducting cable for supplying illumination light to the endoscope 10.

The endoscope 10 comprises a shaft 20, which extends from the proximal end 12 to the distal end 11 of the endoscope. Arranged at the distal end 11 of the endoscope 10 is a pivot prism 30 with a distal light-entry surface 31, a reflective surface 32 and a proximal light-exit surface 33. The pivot prism 30 is embodied, in particular, as Dove/Amici prism and is pivotable about a pivot axis 38 perpendicular to the longitudinal axis of the shaft 20 and perpendicular to the plane of the drawing in FIG. 1. Pivoting the pivot prism 30 about an angle causes pivoting of the viewing direction 14 by twice the angle.

An image transmission device 40 with an optical axis 48 is arranged in the shaft 20. The dash-dotted line which indicates the optical axis 48 of the image transmission device 40 is extended distally as far as the pivot prism 30 and therebeyond in the viewing direction 14 in order to indicate the transmission of light, incident from the viewing direction 14, in the pivot prism 30 and in the image transmission device 40. In particular, the image transmission device 40 is embodied as arrangement of rod lenses, the contours of which are indicated in FIG. 1, or as a different relay lens system. Alternatively, the image transmission device 40 can have a coherent bundle of optical fibers. In this case, the shaft 20 can have a flexible design. Alternatively, a coherent bundle of optical fibers and a relay lens system can be arranged in succession.

An image erecting device 50 is arranged at the proximal end 12 of the endoscope 10, between the proximal end of the image transmission device 40 and the eyepiece 16. While each relay lens system/reversal system causes a complete image reversal, both the reflective surface 32 on the pivot prism 30 and the image erecting device 50 each cause a lateral reversal in a direction in the plane of the drawing in FIG. 1. As a result, the image erecting device 50 lifts the image-inverting effect of the reflective surface 32 of the pivot prism and enables the observation of an erect image through the eyepiece 16.

The endoscope 10 is embodied to surround the pivot prism 30, the image transmission device 40 and the image erecting device 50 in a hermetically sealed manner in order to prevent the ingress into the optical system of water vapor and other fluids and solids with interfering or destructive effect. To this end, the endoscope 10 has, in particular, a curved transparent window component at the distal end 11 and a further transparent window component at the proximal end 12, which are not depicted in FIG. 1.

Figure 2:
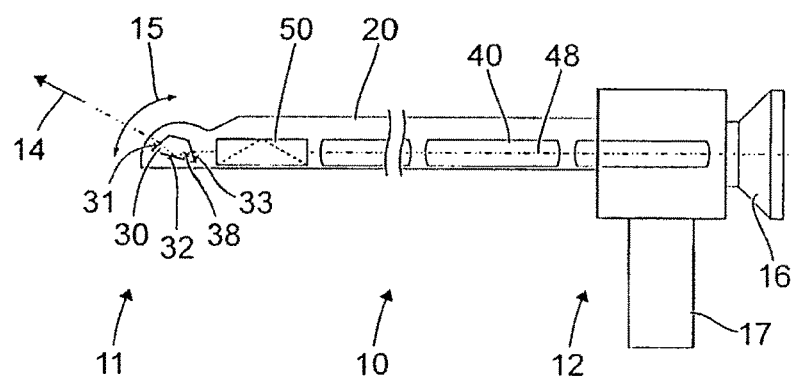
FIG. 2 shows a schematic illustration of a further endoscope with an image erecting device.

FIG. 2 shows a schematic illustration of a further endoscope 10, which is similar in terms of some features and properties to the endoscope depicted above on the basis of FIG. 1. The plane of the drawing in FIG. 2 corresponds to the plane of the drawing in FIG. 1. The following text only describes features and properties by means of which the endoscope 10 from FIG. 2 differs from the endoscope depicted above on the basis of FIG. 1.

Like the endoscope depicted above on the basis of FIG. 1, the endoscope 10 depicted in FIG. 2 likewise has a pivot prism 30 at the distal end, which pivot prism is pivotable about a pivot axis 38 perpendicular to the plane of the drawing in FIG. 2. In order to indicate the effect on the viewing direction 14 of orienting the pivot prism 30, the endoscope 10 in FIG. 2 is depicted with a different viewing direction 14 than the endoscope in FIG. 1.

The endoscope 10 differs from the endoscope depicted above on the basis of FIG. 1 by virtue of, in particular, the fact that the image erecting device 50 is not arranged at the proximal end 12, but close to the distal end 11 of the endoscope, between the pivot prism 30 and the image transmission device 40. The compact design of the image erecting device 50, depicted below on the basis of FIGS. 4 and 5, can enable this distal arrangement of the image erecting device 50, without requiring a significantly enlarged cross section of the shaft 20.

Figure 3:
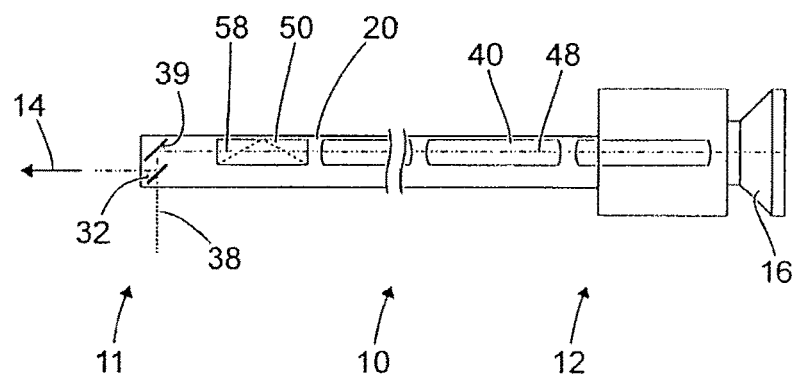
FIG. 3 shows a schematic illustration of a further endoscope with an image erecting device.

FIG. 3 shows a schematic illustration of a further endoscope 10, which is similar to the endoscope depicted above on the basis of FIG. 1 and, in particular, the endoscope depicted above on the basis of FIG. 2 in terms of some features and properties. The following text only describes features and properties of the endoscope 10, in which the latter differs from the endoscope depicted above on the basis of FIG. 2. Although the plane of the drawing in FIG. 3 contains the optical axis 48 of the image transmission device 40, like the planes of the drawing in FIGS. 1 and 2, it is, however, perpendicular to the plane in which the adjustable viewing directions 14 lie and therefore also perpendicular to the planes of the drawing in FIGS. 1 and 2.

The endoscope 10 from FIG. 3 differs from the endoscope depicted above on the basis of FIG. 2 in that, in particular, the fact that a pivotable reflective surface 32 and a fixed reflective surface 39 are provided at the distal end 11 of the endoscope 10. Both the reflective surfaces 32, 39 at the distal end 11 of the endoscope 10 are arranged and embodied to divert or deflect light, in each case by an angle of 90 degrees. The pivotable reflective surface 32 is pivotable about a pivot axis 38, which lies in the plane of the drawing in FIG. 3 and is perpendicular to the optical axis 48 of the image transmission device 40 and perpendicular to the longitudinal axis of the shaft 20. The reflective surface 39 is fixedly arranged.

The surface normal of the pivotable reflective surface 32 in each case includes an angle of 45 degrees with both the viewing direction 14 and with the pivot axis 38. The surface normal of the fixed reflective surface 39 in each case includes an angle of 45 degrees with the pivot axis 38 and with the longitudinal axis 48 of the image transmission device 40. Pivoting of the pivotable reflective surface 32 about an angle brings about pivoting of the viewing direction 14 by the same angle. Deviating from the schematic illustration in FIG. 3, both the pivotable reflective surface 32 and the fixed reflective surface 39 can be embodied on the distal end 11 of the endoscope 10, in each case on a prism or a similar transparent body, within which in each case both the light to be reflected and the reflected light propagates.

Pivoting the pivotable reflective surface 32 at the distal end 11 of the endoscope 10 about the pivot axis 38 thereof causes a rotation of the registered image about the optical axis 48 of the image transmission device 40. A simultaneous rotation of the image erecting device 50 about the rotational axis 58 thereof, which corresponds to the optical axis 48 of the image transmission device 40, reverses this rotation or compensates it.

Figure 4:
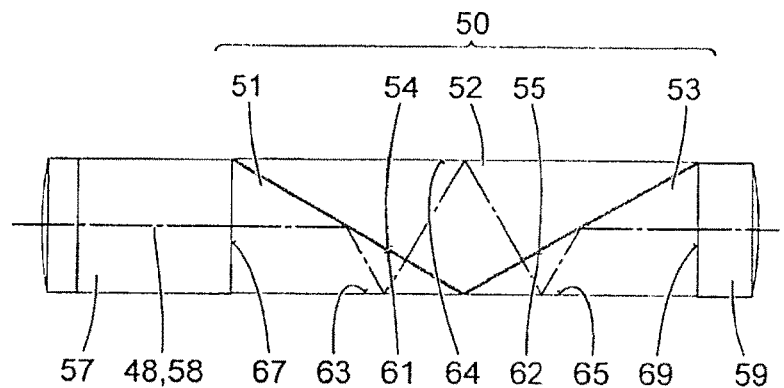
FIG. 4 shows a schematic illustration of an image erecting device.
Figure 5:
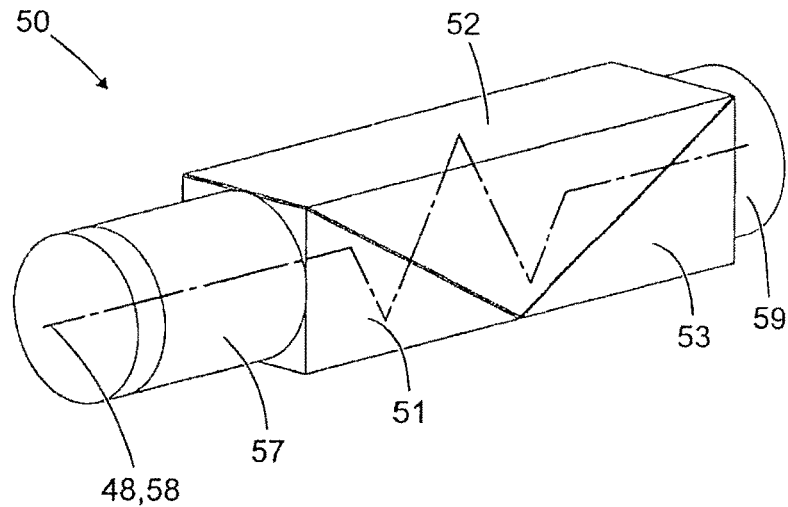
FIG. 5 shows a further schematic axonometric illustration of the image erecting device from FIG. 4.

FIG. 4 shows a schematic illustration of an embodiment of an image erecting device 50 which can be used in the endoscopes depicted above on the basis of FIGS. 1 to 3. The plane of the drawing in FIG. 4 corresponds to the planes of the drawing in FIGS. 1 to 3 and contains the optical axis 48 of the image transmission device 40 (cf. FIGS. 1 to 3) and the rotational axis 58 of the image erecting device 50. FIG. 5 shows a schematic axonometric illustration of the image erecting device 50. The image erecting device 50 is composed of three prisms 51, 52, 53. The first prism 51 and the third prism 53 are similar and arranged in a mirror symmetric manner. The second prism 52 is symmetrically roof-shaped and arranged between the first prism 51 and the third prism 53. Together, the first prism 51, the second prism 52 and the third prism 53 form a substantially cuboid body.

The first prism 51 has a first surface 61 for angle-dependent reflection, which is arranged opposite a light-entry surface 54 of the second prism 52 and parallel thereto. The third prism 53 has a second surface 62 for angle-dependent reflection, which is arranged opposite a light-exit surface 55 of the second prism 52 and parallel thereto. The first prism 51 and the second prism 52 and also the second prism 52 and the third prism 53 are rigidly interconnected in each case, in particular by adhesive bonds in one or more edge regions of the first reflective surface 61 on the first prism 51 and the light-entry surface 54 of the second prism 52 and in one or more edge regions of the second reflective surface 62 on the third prism 53 and the light-exit surface 55 of the second prism 52. Thin spacers, for example in the form of frame-shaped components, which are not depicted in FIGS. 4 and 5 and which ensure predetermined distances between opposing surfaces, are respectively provided between the first reflective surface 61 on the first prism 51 and the light-entry surface 54 of the second prism 52, and also between the second reflective surface 62 on the third prism 53 and the light-exit surface 55 of the second prism 52.

A third surface 63 for angle-independent reflection is provided on the first prism 51. A fourth surface 64 for angle-independent reflection is provided on the second prism 52. A fifth surface 65 for angle-independent reflection is provided on the third prism 53. The third reflective surface 63, the fourth reflective surface 64 and the fifth reflective surface 65 are each mirrored and arranged parallel to one another and to the optical axis 48 of the image transmission device 40 (cf. FIGS. 1 to 3). Furthermore, a light-entry surface 67 of the image erecting device 50 is provided on the first prism 51 and a light-exit surface 69 of the image erecting device 50 is provided on the third prism 53. The light-entry surface 67 and the light-exit surface 69 of the image erecting device 50 each are, in particular, planar and arranged parallel to one another and perpendicular to the optical axis 48.

In the illustrated exemplary embodiment, one circular cylinder 57, 59 made of glass or another transparent material is attached in each case to the light-entry surface 67 and to the light-exit surface 69 of the image erecting device 50. The circular cylinder 57 can be integrally manufactured with the first prism 51 or, for example, joined by adhesive bonding. The circular cylinder 59 can be integrally manufactured with the third prism 53 or, for example, joined by adhesive bonding. The circular cylinders 57, 59 can each be a component of the image erecting device 50, with the form of the image erecting device 50 deviating from the form of a cuboid, at least in the region of the circular cylinders 57, 59. End surfaces of the circular cylinders 57, 59 facing away from the image erecting device 50 are curved, and so, together with the circular cylinders 57, 59, the image erecting device 50 acts like a rod lens which, however, does not cause complete image reversal but merely a lateral reversal in a direction perpendicular to the plane of the drawing in FIG. 4.

By way of example, light passing through the image erecting device 50 from the left-hand side to the right-hand side initially impinges on the first surface 61 for angle-dependent reflection on the first prism 51 and undergoes total internal reflection there due to the large angle with respect to the surface normal (approximately 60 degrees). Thereafter, the light is reflected at the third surface 63 for angle-independent reflection on the first prism 51, passes substantially perpendicularly through the surface 61 for angle-dependent reflection on the first prism and the light-entry surface 54 on the second prism 52, is once again reflected at the fourth surface 64 for angle-independent reflection on the second prism 52, passes substantially perpendicularly through the light-exit surface 55 of the second prism 52 and the second surface 62 for angle-dependent reflection on the third prism 53 and is reflected at the fifth surface 65 for angle-independent reflection. Finally, the light impinges in a flat manner (with an angle with respect to the surface normal of approximately 60 degrees) on the second surface 62 for angle-dependent reflection and undergoes total internal reflection there due to the large angle with respect to the surface normal, in order to leave the image erecting device 50 toward the right-hand side.

In the image erecting device 50, all surfaces involved in the image erecting are perpendicular to the plane of the drawing in FIG. 4. The surface sections of the prisms 51, 52, 53 parallel to the plane of the drawing in FIG. 4 are not involved in the image erecting.

Figure 6:
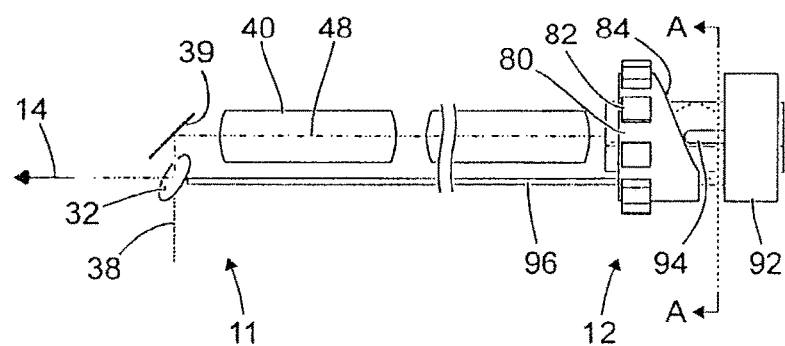
FIG. 6 shows a schematic illustration of parts of an endoscope.

FIG. 6 shows a schematic illustration of parts of an endoscope 10, which is similar in terms of some features and properties to the endoscope depicted above on the basis of FIG. 3. The following text only describes features and properties in which the endoscope 10 differs from the endoscope illustrated above on the basis of FIG. 3.

The plane of the drawing in FIG. 6 corresponds to the plane of the drawing in FIG. 3. However, in contrast to FIG. 3, no external structures of the endoscope, in particular no shaft and no components of a hermetically sealed sleeve around the optical devices, are depicted, and only one part of the optical devices is depicted. Like in the illustrations in FIGS. 1 to 3, FIG. 6 also, for reasons of simplicity, does not show an objective at the distal end 11 of the endoscope 10; the image transmission device 40 is indicated in an exemplary manner by a plurality of rod lenses.

Like in the endoscope depicted above on the basis of FIG. 3, the endoscope 10 shown in FIG. 6 has a fixed reflective surface 39 and a reflective surface 32, pivotable about a pivot axis 38 in the plane of the drawing in FIG. 6, at the distal end 11. In FIG. 6, the pivotable reflective surface 32 is pivoted with respect to the configuration or situation depicted in FIG. 3 by an angle of approximately 20 to 30 degrees about the pivot axis 38, and so the viewing direction 14 does not lie in the plane of the drawing in FIG. 6 but includes a corresponding angle therewith.

In particular, the endoscope 10 differs from the endoscope depicted above on the basis of FIG. 3 in that the image erecting device 50 is arranged at the proximal end 12 of the endoscope 10. The image erecting device 50 corresponds to the image erecting device depicted above on the basis of FIGS. 4 and 5, with glass cylinders 57, 59 (cf. FIGS. 4, 5) on the light-entry surface 67 and on the light-exit surface 69 of the image erecting device 50 not being depicted in FIG. 6 or not being provided in the endoscope 10 depicted on the basis of FIG. 6.

The image erecting device 50 is arranged and held in an approximately ring-shaped magnet support 80, which is also shown in FIG. 7. FIG. 7 shows a schematic sectional illustration of the image erecting device 50 and of the magnet support 80. The sectional plane A-A in FIG. 7 is perpendicular to the plane of the drawing in FIG. 6, to the optical axis 48 of the image transmission device 40 (cf. FIG. 6) and to the rotational axis 58 of the image erecting device 50. The position of the sectional plane A-A is indicated in FIG. 6. In the following text, reference is made to FIGS. 6 and 7.

The approximately ring-shaped magnet support 80 has on the outer circumference thereof a plurality of uniformly arranged magnets 82, the radially outer surfaces of which are alternating north and south poles. All devices depicted in FIGS. 6 and 7 are arranged within a hermetically sealed sleeve (not depicted in FIGS. 6 and 7) which, at least in the region of the magnet support 80, consists of stainless steel or another non-ferromagnetic material. A corresponding magnet support with corresponding magnets, which can be rotated manually, is provided outside of the hermetically sealed sleeve (not depicted here). By coupling the magnets on the manually rotatable magnet support not depicted in FIGS. 6 and 7 and the magnets 82 on the magnet support 80 depicted in FIGS. 6 and 7, a manually produced rotational movement is transferred onto the magnet support 80. The image erecting device 50 is held in an interlocking and force fit and/or cohesive manner in the center of the magnet support 80 by means of a mounting region 85, and connected to the magnet support 80 such that each rotation of the magnet support 80 is accompanied by a corresponding rotation of the image erecting device 50 about the rotational axis 58 (which corresponds to the optical axis 48 of the image transmission device 40).

As can be seen in FIG. 6, the distal edge, which is ring-shaped in the view of FIG. 7, of the magnet support 80 is embodied as a sliding surface 84 which is ramp-shaped in sections. A follower 94 is provided on a slider 92. Furthermore, the slider 92 is connected to the proximal end of a transmission rod 96, the distal end of which is mechanically coupled to the pivotable reflective surface 32 in such a way that a translational movement of the transmission rod 96 in a direction parallel to the longitudinal axis of the shaft 20 (cf. FIGS. 1 to 3) or to the optical axis 48 of the image transmission device 40 is accompanied by a pivot movement of the pivotable reflective surface 32 around the pivot axis 38 thereof. Details of the mechanical coupling between transmission rod 96 and pivotable reflective surface 32 are not depicted in FIG. 6.

The slider 92, the follower 94 and the transmission rod 96 are guided through the devices not depicted in FIGS. 6 and 7 in such a way that they can merely perform translational movements parallel to the optical axis 48 of the image transmission device 40 and to the rotational axis 58 of the image erecting device 50 and of the magnet support 80. By means of a spring (not depicted in FIGS. 6 and 7) or another elastic element, the slider 92 with the follower 94 and the transmission rod 96 is pushed so far in the distal direction (to the left-hand side in FIG. 6) that the distal end of the follower 94 rests against the sliding surface 84 on the proximal side of the magnet support 80. The transmission rod 96 engages through an arcuate slot 86 in the magnet support 80.

Due to the ramp-shaped embodiment of the sliding surface 84 on the magnet support 80, a rotation of the magnet support 80 with the image erecting device 50 about the axis 58 is accompanied by a translational movement of the follower 94, of the slider 92 and of the transmission rod 96, and therefore also by a pivot movement of the pivotable reflective surface 32 at the distal end 11 of the endoscope 10 about the pivot axis 38 thereof. The ramp-shaped sliding surface 84 and the follower 94 form a cam gear which is configured in such a way that the rotation of the registered image produced when pivoting the pivotable reflective surface 32 about the pivot axis 38 thereof is at all times reversed or compensated by the rotation of the image erecting device 50.

FIG. 8 shows a schematic flowchart of a method for erecting an image in an endoscope. Although the method can also be carried out using an endoscope having features and properties deviating from those depicted above on the basis of FIGS. 1 to 7, reference signs from FIGS. 1 to 7 are used below in an exemplary manner to simplify the understanding.

In a first step 101, light (emitted, remitted or reflected light) emanating from an object and entering through a window at the distal end 11 of the endoscope 10 is diverted or deflected. If the object from which the light emanates lies in the viewing direction 14 defined by the orientation of the reflective surface 32, as seen from the distal end 11 of the endoscope 10, the light emanating from the object is coupled into an image transmission device 40.

In a second step 102, the light deflected and coupled into the image transmission device 40 in the first step 101 is transmitted from the distal end 11 to the proximal end 12 of the endoscope 10 by means of the image transmission device 40 (in particular a rod lens system, a different relay lens system and/or a coherent bundle of optical fibers).

In a third step 103, the light is reflected at a first surface 61 for angle-dependent reflection. In a fourth step 104, the light is reflected at a third surface 63 for angle-independent reflection. In a fifth step 105, the light is transmitted through the first surface 61 for angle-dependent reflection or passes through the first surface 61 for angle-dependent reflection. In a sixth step 106, the light is reflected at a fourth surface 64 for angle-independent reflection. In a seventh step 107, the light is transmitted through a second surface 62 for angle-dependent reflection or passes through the second surface 62 for angle-dependent reflection. In an eighth step 108, the light is reflected at a fifth surface 65 for angle-independent reflection. In a ninth step 109, the light is reflected at the second surface 62 for angle-dependent reflection.

The third step 103, the fourth step 104, the fifth step 105, the sixth step 106, the seventh step 107, the eighth step 108 and the ninth step 109 are performed in the sequence described herein. The second step 102 can be performed before the third step 103 or after the ninth step 109.

REFERENCE SIGNS

10 Endoscope
11 Distal end of the shaft 20
12 Proximal end of the shaft 20
14 Viewing direction of the endoscope 10
15 Adjustability of the viewing direction 12 of the endoscope 10
16 Eyepiece of the endoscope 10
17 Coupling for light conducting cables on the endoscope 10
20 Shaft of the endoscope 10
30 Pivot prism at the distal end 11 of the endoscope 10
31 Light-entry surface of the pivot prism 30
32 Pivotable reflective surface at the distal end 11 of the endoscope 10
33 Light-exit surface of the pivot prism 30
38 Pivot axis of the pivot prism 30
39 Fixed reflective surface at the distal end 11 of the endoscope 10
40 Image transmission device in the shaft 20
48 Optical axis of the image transmission device 40
50 Image erecting device
51 First prism of the image erecting device 50
52 Second prism of the image erecting device 50
53 Third prism of the image erecting device 50
54 Light-entry surface of the second prism 52
55 Light-exit surface of the second prism 52
57 Circular cylinder
58 Rotational axis of the image erecting device 50
59 Circular cylinder
61 First surface, for angle-dependent reflection, of the image erecting device 50
62 Second surface, for angle-dependent reflection, of the image erecting device 50
63 Third reflective surface of the image erecting device 50
64 Fourth reflective surface of the image erecting device 50
65 Fifth reflective surface of the image erecting device 50
67 Light-entry surface of the image erecting device 50
69 Light-exit surface of the image erecting device 50
80 Magnet support
82 Magnets on the magnet support 80
84 Sliding surface on the magnet support 80
85 Mounting region for image erecting device 50 on the magnet support 80
86 Slot for transmission rod 96
92 Slider
94 Follower on the slider 92
96 Transmission rod for transmitting a translational movement
101 First step (deflecting light from an object)
102 Second step (transmitting the light)
103 Third step (reflecting the light at a first reflective surface)
104 Fourth step (reflecting the light at a third reflective surface)
105 Fifth step (transmitting the light through the first reflective surface)
106 Sixth step (reflecting the light at a fourth reflective surface)
107 Seventh step (transmitting the light through a second reflective surface)
108 Eighth step (reflecting the light at a fifth reflective surface)
109 Ninth step (reflecting the light at the second reflective surface)

The invention claimed is:

1. An endoscope, comprising:
an image transmission device in a shaft for transmitting an image from the distal end to the proximal end of the endoscope;
an image erecting device in the shaft for erecting an image registered by means of the endoscope;
the image erecting device having a first reflective surface extending in a first plane for angle-dependent reflection, and a second reflective surface extending in a second plane for angle-dependent reflection, the second plane being oriented non-parallel relative to the first plane; and
the image erecting device being configured such that light for image erecting is successively reflected at the first reflective surface, passed through the first reflective surface, passed through the second reflective surface, and reflected at the second reflective surface;

wherein the image erecting device defines at least a substantially cuboid shape that encompasses the first and second reflective surfaces, the image erecting device having a cross-section in a plane perpendicular to an optical axis of the image transmission device that is at least substantially square shaped.

2. The endoscope according to claim 1, wherein the image erecting device is configured such that light for image erecting is successively reflected at the first reflective surface, reflected at a third reflective surface, passed through the first reflective surface, reflected at a fourth reflective surface, passed through the second reflective surface, reflected at a fifth reflective surface and reflected at the second reflective surface.

3. The endoscope according to claim 2, wherein the third reflective surface and the fifth reflective surface are arranged parallel to one another.

4. The endoscope according to claim 2, wherein the third reflective surface, the fourth reflective surface, and the fifth reflective surface are arranged parallel to the optical axis of the image transmission device.

5. The endoscope according to claim 2,
wherein a light-entry surface of the image erecting device and a light-exit surface of the image erecting device are arranged on two planar surface sections, lying opposite one another, of six planar surface sections of the image erecting device; and
wherein the fourth reflective surface, on the one hand, and the third and the fifth reflective surface, on the other hand, are arranged on two further planar surface sections, lying opposite one another, of the six planar surface sections of the image erecting device.

6. The endoscope according to claim 2, wherein the image erecting device comprises a first prism, a second prism, and a third prism;
wherein the first prism comprises a light-entry surface of the image erecting device, the first reflective surface, and the third reflective surface;
wherein the second prism comprises the fourth reflective surface, a light-entry surface which is opposite and parallel to the first reflective surface, and a light-exit surface which is opposite and parallel to the second reflective surface; and
wherein the third prism comprises a light-exit surface of the image erecting device, the second reflective surface, and the fifth reflective surface.

7. The endoscope according to claim 1, wherein the first reflective surface and the second reflective surface of the image erecting device are each arranged at an angle of 30 degrees with respect to the optical axis of the image transmission device.

8. The endoscope according to claim 1, further comprising:
a further reflective surface at the distal end of the endoscope, for coupling light, emanating from an object to be observed, into the image transmission device, the further reflective surface being pivotable about a pivot axis for adjusting the viewing direction; and
a device for coupling the image erecting device with the further reflective surface in such a way that pivoting the further reflective surface about the pivot axis is accompanied by a rotation of the image erecting device about a rotational axis parallel to the optical axis of the image transmission device.

9. A method for erecting an image in an endoscope, comprising the following successive steps:
providing an image erecting device for erecting an image registered by the endoscope, the image erecting device having a first reflective surface extending in a first plane for angle-dependent reflection, and a second reflective surface extending in a second plane for angle-dependent reflection, the second plane being oriented non-parallel relative to the first plane, the image erecting device defines at least a substantially cuboid shape that encompasses the first and second reflective surface, the image erecting device having a cross-section in a plane perpendicular to an optical axis of the image transmission device that is at least substantially square shaped;
reflecting light emanating from an object to be observed at the first reflective surface;
transmitting the light through the first reflective surface for angle-dependent reflection;
transmitting the light through the second reflective surface; and
reflecting the light at the second reflective surface for angle-dependent reflection.

10. The endoscope according to claim 2, wherein the third reflective surface and the fifth reflective surface are co-planar.

11. The endoscope according to claim 6, wherein the first reflective surface, the second reflective surface, the light-entry surface of the second prism, and the light-exit surface of the second prism are of a same size.

12. The endoscope according to claim 1, wherein the image erecting device comprises a first prism, a second prism, and a third prism;
wherein the first prism comprises the first reflective surface, and the third prism comprises the second reflective surface; and
wherein the second prism extends in a direction between the first reflective surface and the second reflective surface.

13. The endoscope according to claim 1, wherein the first reflective surface abuts a surface other than the second reflective surface.

14. The endoscope according to claim 1, wherein the image erecting device has a length extending along a first portion of an optical path of the endoscope and a height extending in a direction perpendicular to the optical path, the height of the image erecting device being uniform along the length of the image erecting device;
wherein the image transmission device includes a rod lens having a length extending along a second portion of the optical axis and a height extending in a direction perpendicular to the optical path, the height of the rod lens being uniform along the length of the rod lens; and
wherein the height of the image erecting device and the height of the rod lens are substantially equal.

* * * * *